United States Patent [19]

Smith

[11] Patent Number: 5,209,801
[45] Date of Patent: May 11, 1993

[54] METHOD OF FORMING A DISPOSABLE ELASTIC STRUCTURE

[75] Inventor: Carol L. Smith, Federal Way, Wash.

[73] Assignee: Weyerhaeuser Company, Tacoma, Wash.

[21] Appl. No.: 742,223

[22] Filed: Aug. 6, 1991

Related U.S. Application Data

[63] Continuation of Ser. No. 472,600, Feb. 20, 1990, abandoned, which is a continuation of Ser. No. 245,492, Sep. 19, 1988, Pat. No. 4,977,011.

[51] Int. Cl.⁵ .......................... B32B 3/22; B32B 5/04; B32B 5/12; B32B 5/26; B32B 7/14
[52] U.S. Cl. ........................................ 156/161; 2/181; 2/DIG. 11; 156/177; 156/179; 156/183; 156/229; 156/291; 156/301; 428/109; 428/112; 428/152; 428/201; 428/286; 602/41; 602/62; 602/75; 602/900; 604/308; 604/385.1
[58] Field of Search ............. 2/181, DIG. 1; 156/161, 156/177, 179, 183, 229, 291, 301; 428/109, 112, 152, 201, 286; 604/308, 385.1; 602/41, 62, 75, 900

[56] References Cited

U.S. PATENT DOCUMENTS

| | | | |
|---|---|---|---|
| 1,949,159 | 11/1932 | Glidden et al. | 428/231 |
| 2,341,019 | 2/1944 | Cook | 428/231 |
| 3,297,514 | 1/1967 | Poeschl et al. | 428/230 |
| 3,316,136 | 4/1967 | Pufahl | 156/160 |
| 3,371,668 | 3/1968 | Johnson | 604/366 |
| 3,575,782 | 4/1971 | Hansen | 428/293 |
| 4,548,859 | 10/1985 | Kline et al. | 428/251 |
| 4,552,795 | 11/1985 | Hansen et al. | 428/110 |
| 4,582,550 | 4/1986 | Sigl | 156/84 |
| 4,606,964 | 8/1986 | Wideman | 428/152 |
| 4,640,859 | 2/1987 | Hansen et al. | 428/105 |
| 4,683,877 | 8/1987 | Ersfeld et al. | 128/90 |
| 4,734,311 | 3/1988 | Sokolowski | 428/152 |
| 4,756,942 | 7/1988 | Aichele | 428/102 |
| 4,863,779 | 9/1989 | Daponte | 428/152 |
| 4,977,011 | 12/1990 | Smith | 428/152 |
| 4,984,584 | 1/1991 | Hansen et al. | 128/898 |

FOREIGN PATENT DOCUMENTS

| | | |
|---|---|---|
| 120117 | 10/1984 | European Pat. Off. |
| 299438 | 1/1989 | European Pat. Off. |
| 1563498 | 4/1069 | France |

Primary Examiner—James C. Cannon
Attorney, Agent, or Firm—Klarquist, Sparkman, Campbell, Leigh & Whinston

[57] ABSTRACT

This invention teaches a method of forming a low cost, breathable, light weight, soft, disposable elastic structure with surface properties that are characterized by a controlled irregularity of the pleats or shirrs that make up the broad surfaces of the structure. The structure is a layered structure with outer layers of low basis weight breathable material, a central elastic layer, and an adhesive layer that serves to join all the layers together to form a unitary elastic structure.

26 Claims, 5 Drawing Sheets

METHOD OF FORMING A DISPOSABLE ELASTIC STRUCTURE

This application is a continuation of application Ser. No. 07/472,600, filed on Feb. 20, 1990, now abandoned, which was a continuation of application Ser. No. 07/245,492, filed on Sep. 19, 1988, and now issued as U.S. Pat. No. 4,977,011.

FIELD OF THE INVENTION

This invention relates to low cost breathable elastic structures.

More particularly, this invention relates to elastic structures as described above wherein the structure has a first layer of breathable material, a second layer of breathable material positioned parallel to the first layer and a multiplicity of elastic strands positioned between the two layers and the layers and the strands are joined together to form a substantially unitary structure wherein the elastic strands draw the breathable layers into pleated contractions such that when the pleats are drawn apart the structure has resilient elastic properties.

BACKGROUND OF THE INVENTION

Elastic structures such as sweat bands, bandages, athletic supporters, support straps for incontinence devices and the like are often soiled on their first use and become unpleasant to deal with. The preferred method of dealing with these soiled structures would be to discard them. In most instances the cost of the elastic structure is such that it is not ordinarily economically practical to discard the elastic structure after a single use.

The art has long sought after a low cost disposable elastic structure.

For example, it is a general practice for the manufacturers of absorbent shields for incontinent care to provide a disposable shield to which reuseable support straps are attached. Attached straps that are disposable with the shield would be highly desirable but this has not heretofore been economically possible.

Breathability in an elastic structure is seen as being highly desirable. A breathable elastic bandage would promote healing. A breathable elastic support structure would be cooler to wear than existing elastic support structures.

Presently available elastic structures of the type contemplated by this invention are somewhat stiff and often have a harsh and irritating surface texture.

Presently available elastic structures of the type contemplated by this invention generally have a uniform surface texture and a uniform degree of elasticity throughout the structure.

OBJECTS

It is, therefore, an object of this invention to provide a breathable elastic structure that is sufficiently low in cost to permit the discarding of the structure after a single use and sufficiently durable to permit multiple uses.

It is further an object of this invention to provide the structure described above wherein the structure is flexible and is provided with a multi-textured surface that is soft and comfortable when worn in direct contact with the skin of a user.

It is further an object of this invention to provide the structure described above wherein the direction and magnitude of the elastic properties of the structure may be varied for different areas of the structure to provide a high degree of tension where needed and a lower degree of tension where low tension is desirable.

Other objects will become apparent from the following specifications, drawings, and claims.

BRIEF DISCUSSION OF THE PRIOR ART

The relevant patent art of which the inventor is aware is as follows:

| PATENT NO. | INVENTOR | DATE |
|---|---|---|
| 1,949,159 | Glidden et al | February 27, 1934 |
| 2,341,019 | Cook | February 8, 1944 |
| 3,297,514 | Poeschl et al | January 10, 1967 |
| 3,316,136 | Pufahl | April 25, 1967 |
| 4,548,859 | Kline et al | October 22, 1985 |
| 4,552,795 | Hansen et al | November 12, 1985 |
| 4,683,877 | Ersfeld et al | August 4, 1987 |

If described broadly, the prior art can be seen to provide or teach many of the elements of the instant invention.

Glidden teaches a breathable structure having an elastic central element and breathable material adhered to the top and bottom surfaces of the elastic structure.

Cook teaches the intermittent attachment of elastic strands to extensible material.

Poeschl teaches elastic strands bonded between layers of fabric. Pufahl teaches the employment of resilient elements to form a contoured structure.

Kline teaches a method of forming a breathable extensible structure.

Hansen teaches the employment of an elastic member to create a pleated or shirred elastic structure.

Ersfeld teaches the use of extensible materials to form a support for a body member.

However, the prior art cannot be fairly characterized as teaching the instant invention or rendering it obvious.

None of the prior art structures make any claim to being sufficiently low in cost so that they would be economically disposable after a single use in one of the product forms described above in the discussion of the background of the invention.

None of the prior art references nor any reasonable combination of the prior art references would lead one skilled in the art to the means employed in the instant invention to achieve an elastic structure having a controlled nonuniformity of surface properties.

BRIEF DESCRIPTION OF THE INVENTION

The invention in its simplest form is characterized by being a layered structure having a first outer breathable layer, a central layer of a multiplicity of nonintersecting elastic strands, a second outside breathable layer and the layers are joined together to form a substantially unitary structure. The structure is achieved by forming a layer of nonintersecting elastic strands, tensioning the strands, positioning the tensioned strands between two layers of breathable material, joining the layers together, and releasing the tension in the strands and thereby permitting them to contract and draw the outer layers into pleats or shirrs. The nonintersecting elastic strands are typically configured so that they are slightly out of parallel and/or irregularly spaced and/or nonuniformly tensioned so as to cause the pleats to form slightly irregularly.

DETAILED DESCRIPTION OF THE INVENTION

In the figures, like numbers refer to like objects, pleats are shown semi-schematically, and the thickness of some elements have been exaggerated for clarity of disclosure.

Figure 1:
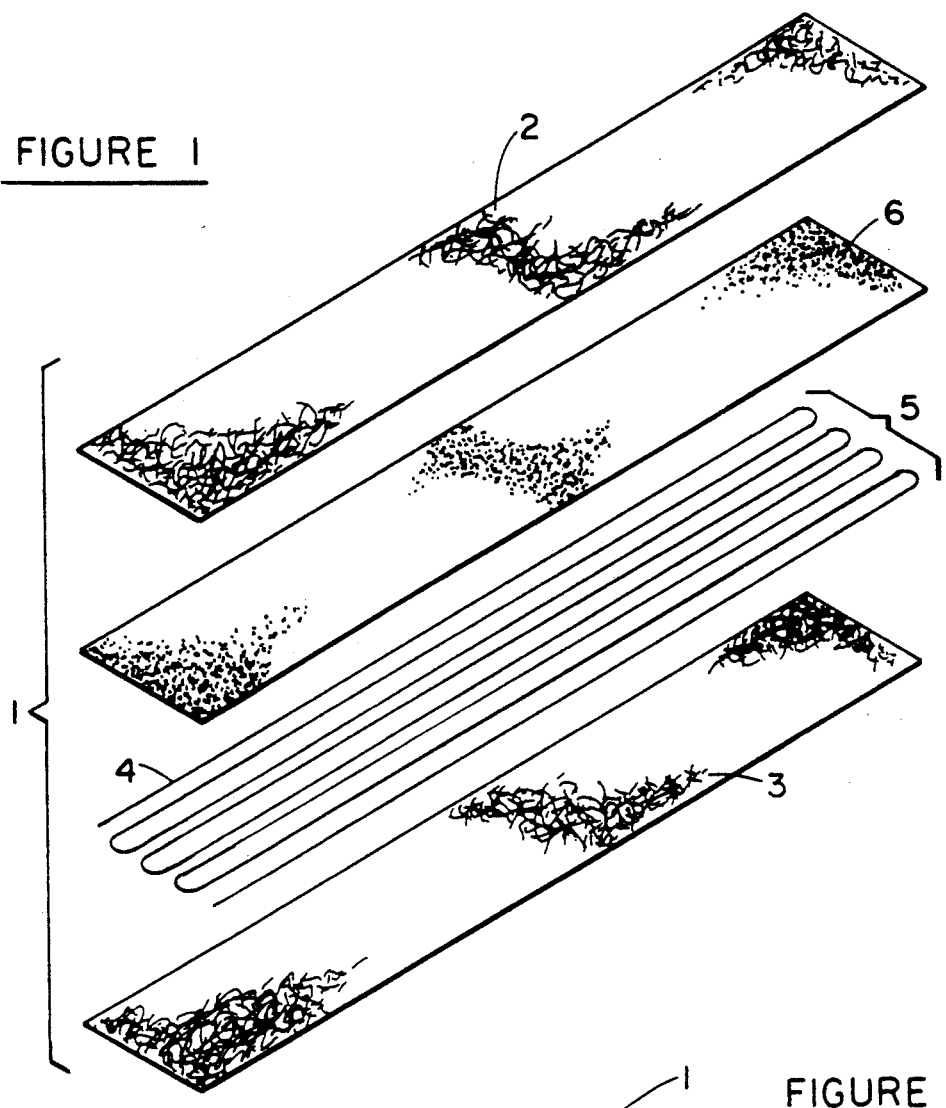
FIG. 1 is an exploded pictorial view showing the relationships between the elements of an elastic structure made according to this invention.
Figure 2:
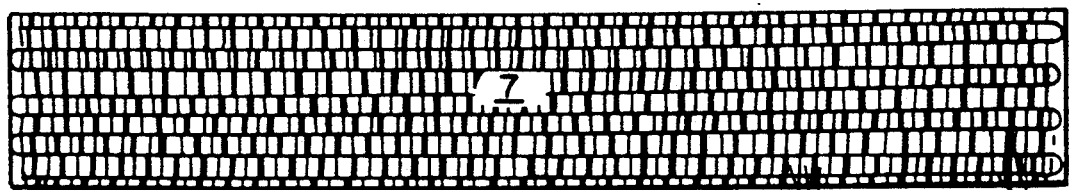
FIG. 2 is a plan view of the elastic structure of FIG. 1 in completed form.

Referring now to FIGS. 1 and 2 which show a strap or band, elastic structure 1, such as might be used in a sweat band or the support system for a perineal shield. First nonwoven layer 2 and second nonwoven layer 3 are of a low basis weight breathable nonwoven material. The term "low basis weight" as used herein shall be read to means a basis weight less than 40 grams per square meter. A 23.5 grams per square meter basis weight nonwoven material sold by James River Corporation, of Simpsonville, S.C. under the name of APN 185 thermal bond polypropylene is representative of the type of material that has been found to be satisfactory for forming elastic structure 1.

Elastic strand 4 is shown as a single strand that is laid to form an elastic layer 5 of a multiplicity of nonintersecting lines of elastic. Multiple strands of elastic have been found to be satisfactory in fabricating elastic structure 1. Elastic strands such as the 1240 decitex (DTEX) elastic strand sold by E. I. DuPont de Nemours & Co. of Maitland, Ontario, Canada under the name of Lycra (TM) T-126 is representative of the elastic stranding that has been found to be serviceable in forming elastic structure 1.

Adhesive layer 6 is shown as a continuous thin layer of adhesive such as the two sided tape adhesive provided by the 3M Company of Minneapolis, Minn. under the Scotch Tape (TM) brand name. Adhesive layer 6 may be achieved by spraying, printing, extruding or the like, an open or patterned layer of adhesive, such as Findley 995372 sold by the Findley Corp. of Wauwatosa Wis., on one of the nonwoven layers. The thin film of adhesive used to form adhesive layer 6 of FIG. 1 will, when elastic strands 4 are contracted, be caused to separate and create small openings in sufficient number to render elastic structure 1 breathable.

Elastic structure 1 as described above is light in weight, soft in texture, breathable, and sufficiently low in cost to be disposable after a single use. Because prices and costs and product specifications are subject to frequent change, it is not possible to define "low cost" with any precision. However, the following example will provide a sense for the degree to which the materials costs for the an elastic structure made according to this invention are below the materials costs of similar prior art elastic structures.

EXAMPLE 1

| Elastic structure | Support Strap For Perineal Shield. |
| --- | --- |
| Relaxed Length | 15.24 Centimeters |
| Stretched Length | 38.18 Centimeters |
| Width | 2.54 Centimeters |
| Total Weight | 1.05 Grams |
| Nonwoven cost/strap | 0.15 Cents |
| Elastic cost/strap | 0.21 Cents |
| Adhesive cost/strap | 0.22 Cents |
| Total Components cost/strap | 0.58 Cents |

A materials cost of 0.58 cents per strap indicates that it is not unreasonable to consider such an elastic structure to be a disposable product.

The light weight attribute of elastic structure 1 is a result of the the sums of the light weights of each of the components in the structure.

The softness of the strap is achieved by interaction of the components in the novel construction of the elastic structure of this invention. As illustrated in FIG. 2, the texture of surface 7 of elastic structure 1 has a nonuniformity that is regularly distributed and maintained between distinct limits. The low basis weight nonwoven layers 2 and 3 easily flex into soft pleats that are in clear distinction to the harsh knuckle like pleats that characterize prior art elastic structures having higher basis weight components. The controlled nonuniformity of surface 7 eliminates many of the pressure lines that characterize prior art elastic structures. This controlled nonuniformity of surface 7 can be obtained by several methods or by combinations of these methods.

Figure 3:
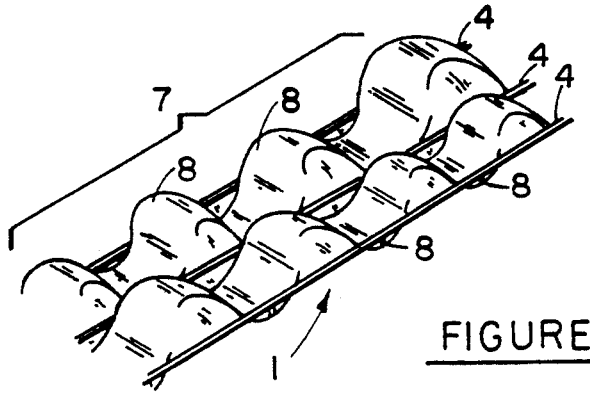
FIG. 3 is a fragmentary pictorial view illustrating the forming of pleats according to this invention.

In FIGS. 1 through 3, the positioning of nonintersecting strands 4 in nonparallel relationship to each other is illustrated. A typical elastic structure 1 might have 4 to 12 strands of elastic per transverse inch positioned so that the strands converge or diverge over their length by approximately 0.017 inches. The shirrs or pleats 8 that form when elastic strands 4 contract, change both period and amplitude along the lengths of strands 4 as strands 4 converge or diverge, with the result that the pleats 8 to one side of a strand 4 are not ordinarily of the same amplitude or period as the pleats on the other side of a strand 4. This controlled irregularity of pleats 8 of elastic structure 1 eliminates transverse gathers that in prior art elastic structures create transverse pressure lines and folds that can pinch skin and pull hairs.

A controlled irregularity of surface 7 of elastic structure 1 may be achieved by providing unequal tensions to elastic strands 4 or by applying adhesive layer 6 in patterns that produce irregularities in the bond points along an elastic strand 4. These methods of providing controlled irregularity to surface 7 of elastic structure 1 may be employed singly or in combinations.

Figure 4:
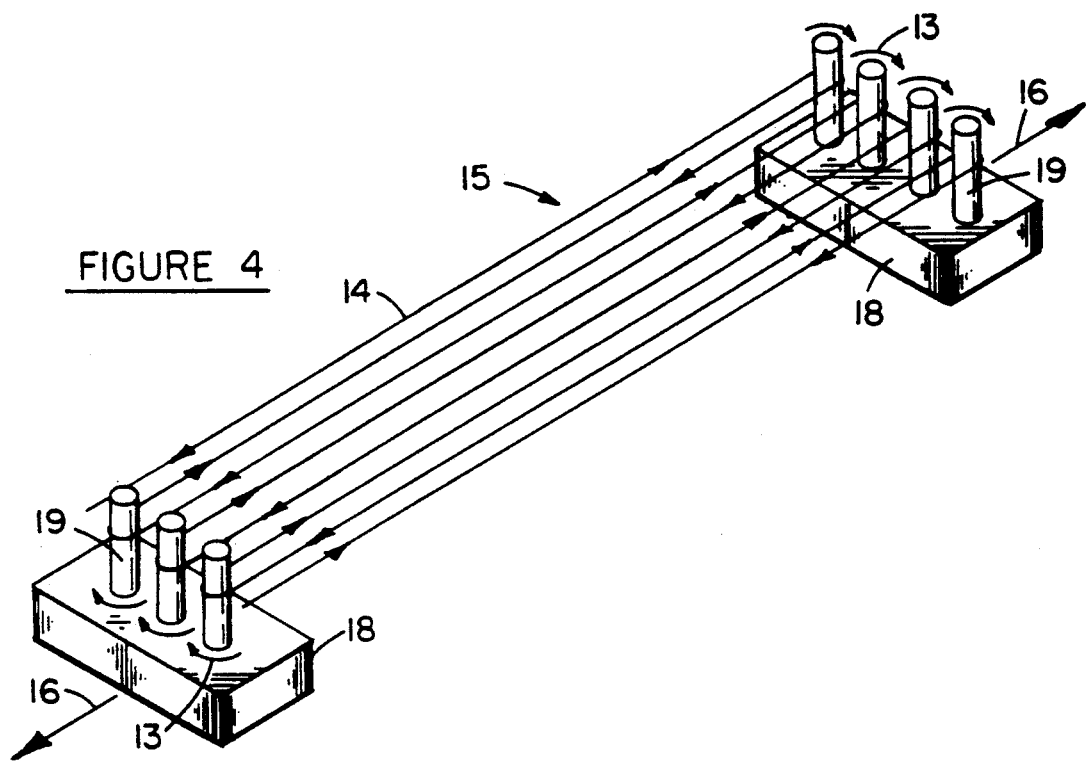
FIG. 4 is a pictorial view illustrating a means for imparting differing tensions to alternate segments of an elastic strand.
Figure 5:
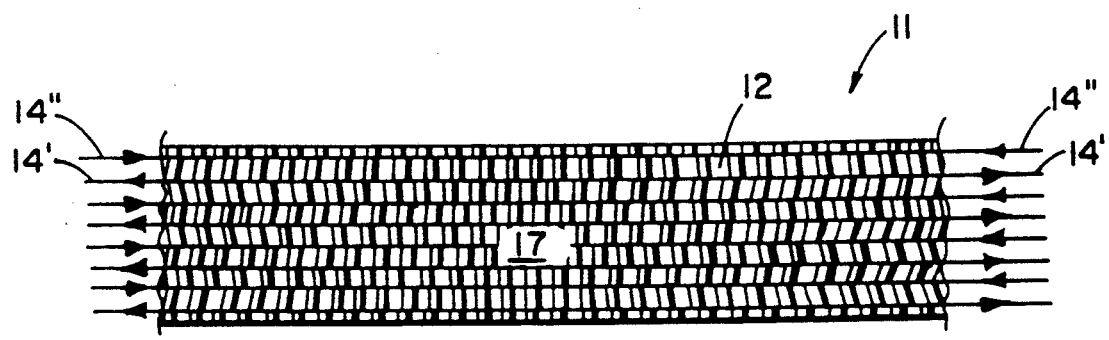
FIG. 5 is a fragmentary pictorial view showing a portion of the surface of another elastic structure made using the means of FIG. 4.

Referring now to FIGS. 4 and 5, wherein elastic layer 15 is similar to elastic layer 5 and elastic structure 11 is similar to elastic structure 1 and surface 17 is similar to surface 7 and elastic strands 14 and 14' and 14" are similar to elastic strands 4. Strand 14 is reciprocally woven about pins 19 and given a uniform unstretched tension. Pin blocks 18 are then caused to diverge as shown by arrows 16. Pins 19 are then caused to rotate as shown by arrows 13. The tension in strands 14' is thereby caused to increase while the tension in strands 14" is caused to decrease. Elastic layer 15 is then incorporated in elastic structure 11 by means similar to those recited in relation to FIGS. 1 through 3. When the tension in strands 14' and 14" is released, the pleats 12 formed between strands 14' and 14" have a different period and amplitude adjacent to strands 14' than they do adjacent to strands 14". Surface 17 is thereby given a controlled irregularity and freedom from transverse pressure lines analogous to that of surface 7 of FIGS. 1 through 3.

The use of alternate elastic strands having different elastic properties to achieve the ends achieved in the embodiments of FIGS. 4 and 5 is within the scope of this invention.

Figure 6:
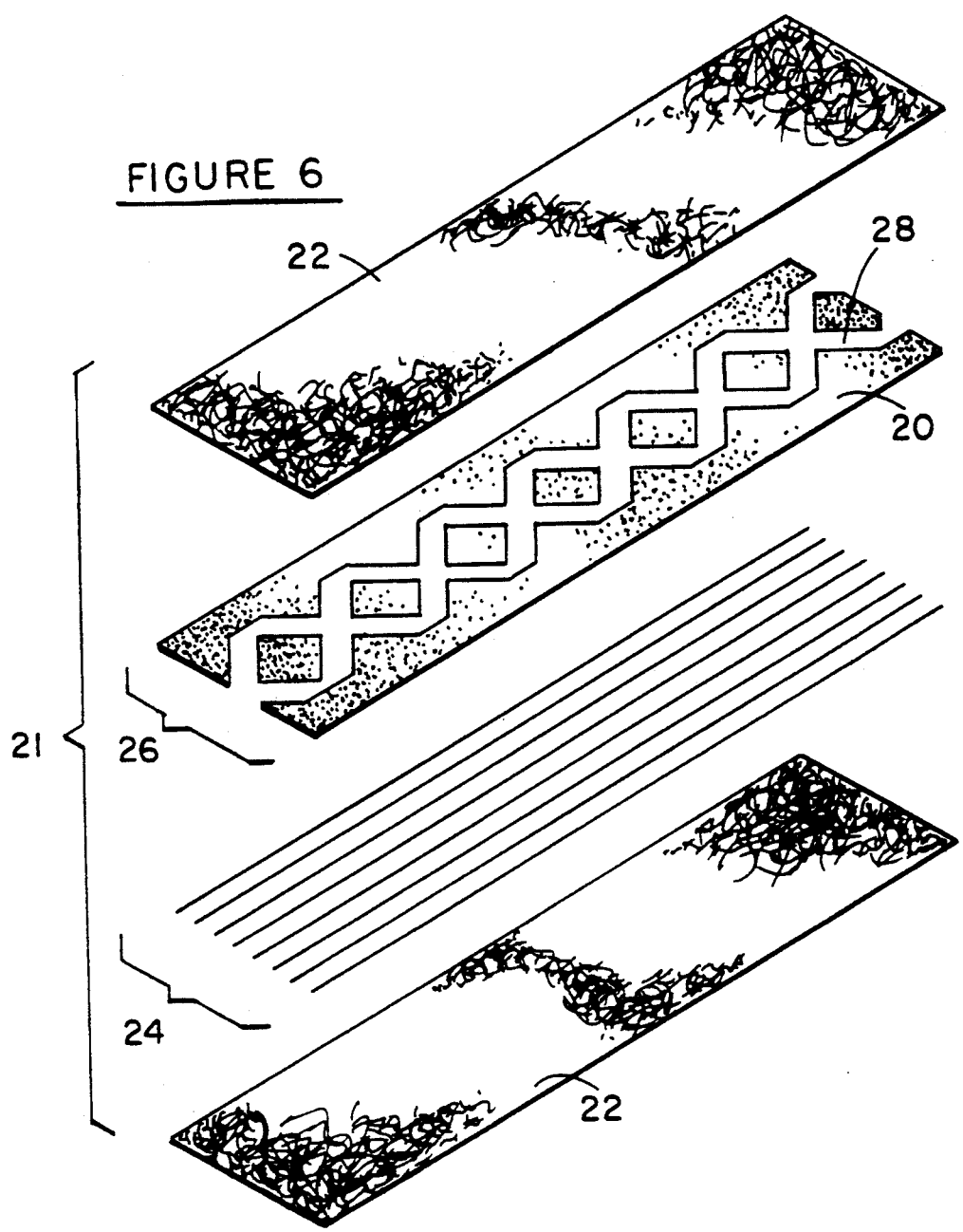
FIG. 6 is an exploded pictorial view illustrating a patterned adhesive layer used in forming a structure.
Figure 7:
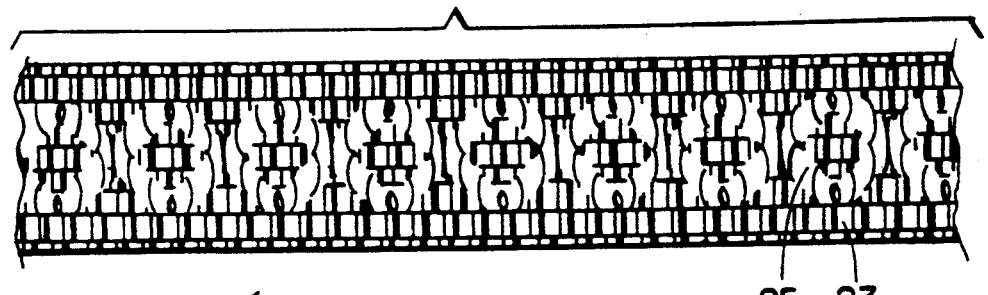
FIG. 7 is a fragmentary plan view of the surface of an ; elastic structure formed using the adhesive layer of FIG. 6.

Referring now to FIGS. 6 and 7 wherein a controlled irregularity is provided to surface 27 by means of an adhesive layer 26 being given a pattern of adhesive 20 interspersed with open areas 28. When adhesive layer 26 is applied to a nonwoven layer 22 and an elastic structure 21 similar to elastic structure 1 is formed, and elastic strands 24 are contracted, the adhered portions of elastic structure 21 form relatively short period and low amplitude pleats 23 and the unadhered areas form relatively irregular and relatively high amplitude pleats 25. Numerous useful and beneficial patterns of adhesive 20 may be used to form adhesive layer 26. It is well known in the art to provide such patterns of adhesive by spraying, screen printing, and the like.

It should be noted that in the embodiment of FIGS. 6 and 7 that the unadhered areas of surface 27 provide a degree of breathability and a method of providing breathability to elastic structures of this invention that has not heretofore been available in the art.

Elastic structures 1, 11, and 21 described above are strap-like structures characterized by elasticity in one direction and inelasticity transverse to the direction of elasticity. It is within the scope of this invention to provide the novel combinations of properties of the elastic structure of this invention to elastic structures having multi-directional elasticity.

Figure 8:
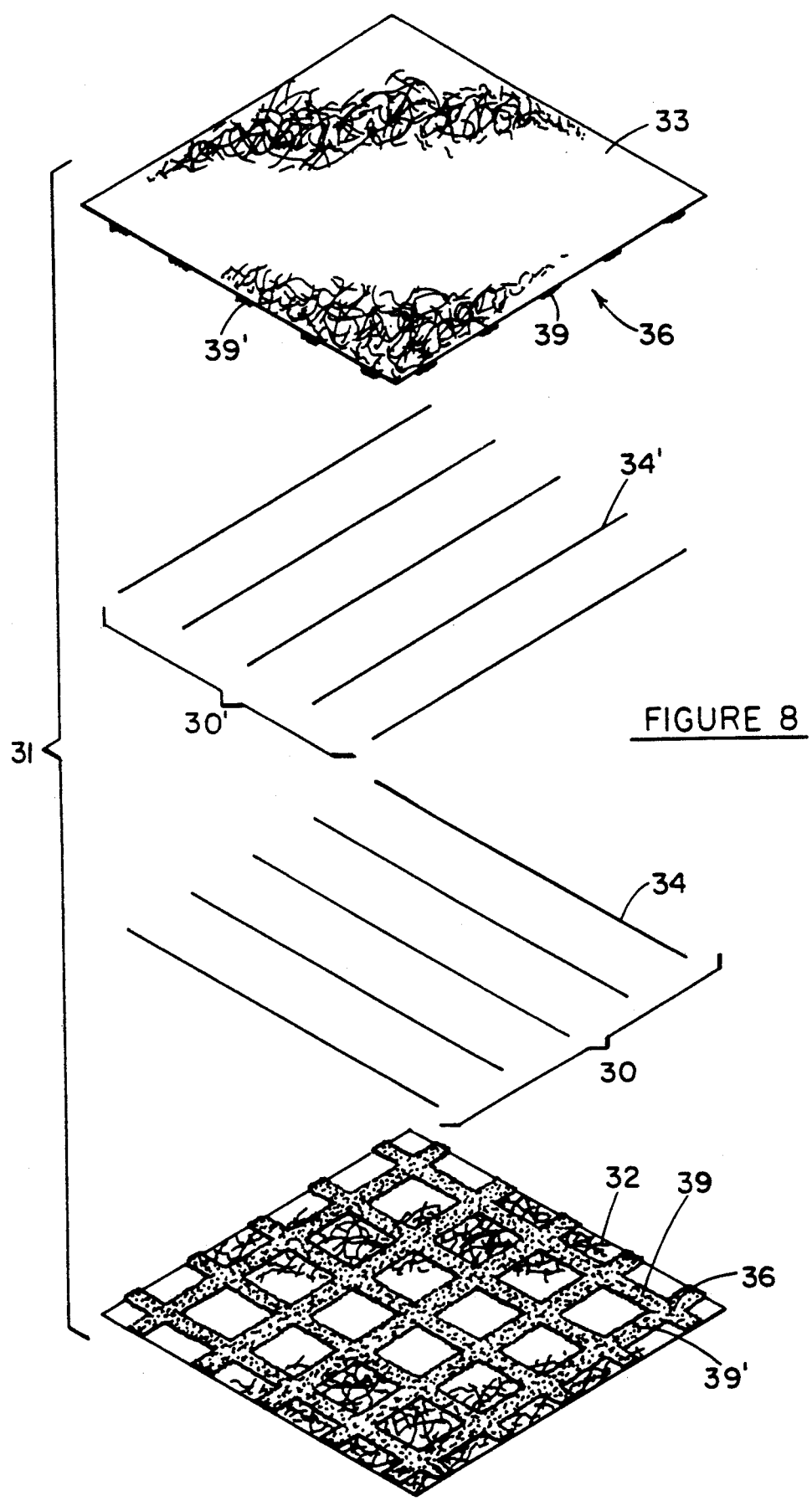
FIG. 8 is an exploded pictorial view illustrating the relationship between the components of a multi-directional elastic structure made according to this invention.
Figure 9:
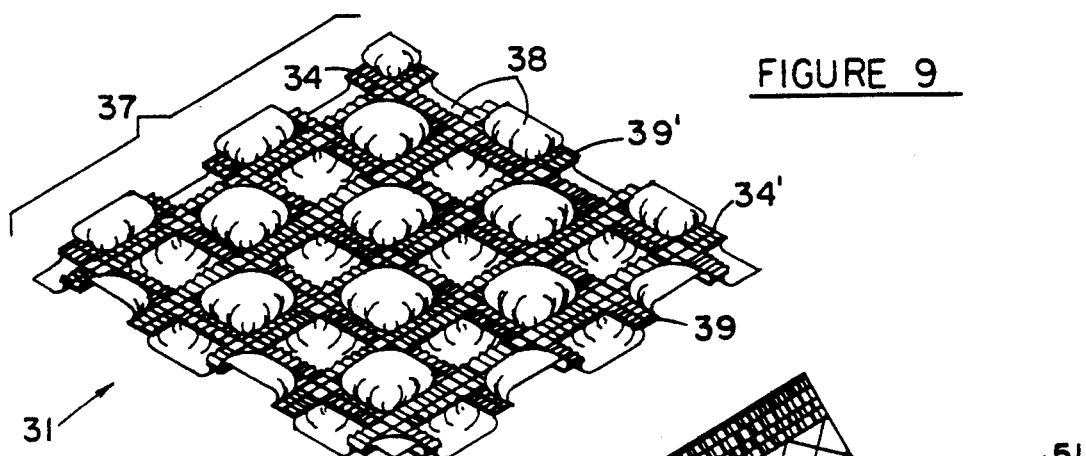
FIG. 9 is a pictorial view sowing a portion of the elastic structure of FIG. 8 in finished form.

Referring now to FIGS. 8 and 9 wherein a multi-directional elastic structure is shown. Elastic structure 31 has first nonwoven layer 32, adhesive layer 36 formed in a pattern of rectangles applied to first nonwoven layer 32, first elastic layer 30 configured so that tensioned strands 34 will lie along first parallel elements 39 of adhesive layer 36, second elastic layer 30' configured so that tensioned strand 34' will lie along second parallel elements 39' of adhesive layer 36 and second nonwoven layer 33. When the elements of elastic structure 31 are adhered together to form a substantially unitary structure and the tensions in strands 34 and 34' are released elastic structure 31 takes the form shown in FIG. 9. Pleats 38 that make up surface 37 are soft and breathable.

Elastic structure 31 is soft, light weight, breathable, multi-directional in elasticity and inexpensive enough to be disposable after a single use. The tensioning in tensioned strands 34 and 34' may be altered to give elastic structure 31 different elastic properties in different directions. The angle between first parallel elements 39 and second parallel elements 39' of adhesive layer 36 may be any chosen angle to give elastic structure 31 multi-directional elastic properties of the user's choosing.

Figure 10:
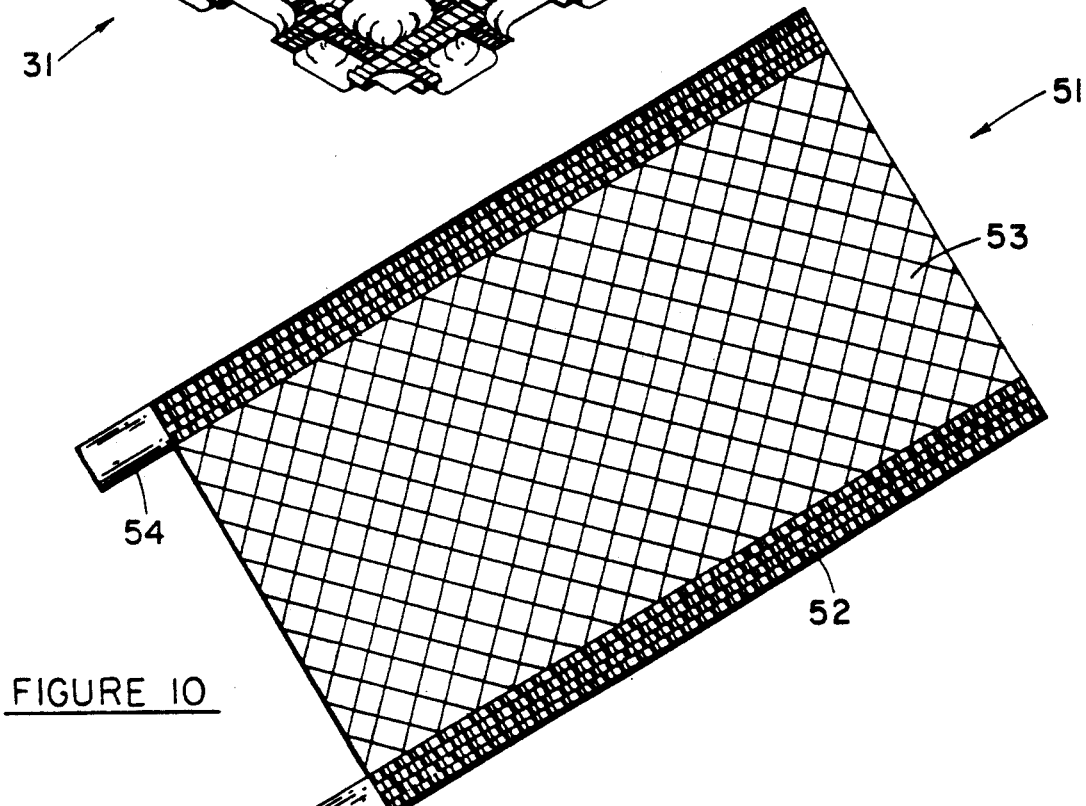
FIG. 10 is a plan view of an elastic support structure made according to this invention.
Figure 11:
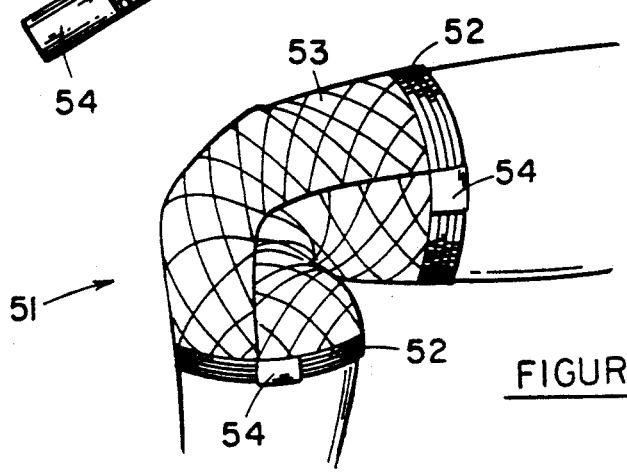
FIG. 11 is a pictorial view of the elastic support structure of FIG. 10 in place on a knee joint.

Referring now to FIGS. 10 and 11 wherein a breathable support structure for a body joint is shown. Elastic support structure 51 has uni-directional side straps 52, multi-directional midspan 53, and closures 54. Elastic support structure 51 is breathable and liquid permeable and may serve to retain a wetable compress in position for treating injured joints such as knees, elbows, and the like. Support structure 51 serves to illustrate the combining of uni-directional elastic structures of this invention with multi-directional elastic structures of this invention to create versatile low cost elastic structures.

Nonwovens are typically given a nominal basis weight in grams per square meter. If random samples of 2 square centimeters are taken from a square meter of nonwoven, they will show a variance from the nominal basis weight of the nonwoven. This distributed controlled variance of basis weight along with associated variances in the number of bond points present in small areas contribute to producing a controlled variance in the pleating of the surfaces of an elastic structure made according to this invention. By using nonwovens of a predetermined range of variance in basis weight and/or bonding distributions the elastic structures 1, 11, 21, 31, and 51 may be provided with a surface having a degree of controlled nonuniformity that is attributable to controlled nonuniformity in the nonwoven breathable outer layers used to form the elastic structures.

The above disclosures and descriptions would enable one skilled in the art to make and use the elastic structures of this invention without undue experimentation. The best modes of practicing the invention known to the inventor have been disclosed. However, it is obvious that very many combinations and variations of the elements of this invention may be had, beneficially, without departing from the scope of the invention. To recite all these combinations and variations would greatly multiply the drawings and claims and cause the specifications to become prolix.

Therefore, it should be understood that the scope of the invention should not be limited to the embodiments disclosed, but that the scope of the invention should be limited only by the scope of the appended claims and all equivalents thereto that would become apparent to one skilled in the art.

I claim:

1. A method of forming a breathable elastic structure having substantially unidirectional elastic properties, comprising the steps of:
   providing a nonwoven low basis weight first breathable outside layer, a nonwoven low basis weight second breathable outside layer, and a first elastic layer having a multiplicity of nonintersecting elastic strands;
   stretching the first elastic layer by stretching the nonintersecting elastic strands of the first elastic layer;

positioning the stretched nonintersecting elastic strands of the first elastic layer between the first and second outside layers;

adhering the first and second outside layers together with the stretched first elastic layer therebetween to form a substantially unitary structure; and forming a breathable elastic structure having a nonuniformity which is substantially regularly distributed throughout the elastic structure, the forming step comprising the step of relaxing the stretching of the first elastic layer to cause the first elastic layer to contract and to draw the outside layers into pleats having a controlled irregularity with the pleats on opposing sides of each elastic strand substantially having different periods and amplitudes, and the pleats, when drawn apart, having substantially unidirectional elastic properties so as to allow the elastic structure to be drawn apart in a direction substantially parallel with at least one the nonintersecting elastic strands.

2. A method of forming a breathable elastic structure according to claim 1 wherein the providing step comprises providing first and second outside layers of a nonwoven material having a nominal basis weight of less than 40 grams per square meter, with the basis weight having a distributed controlled variance, and with the regularly distributed nonuniformity of the elastic structure being attributable at least in part to the distributed controlled variance of the basis weight of the outside layers.

3. A method of forming a breathable elastic structure according to claim 1 further comprising the step of forming the structure into a sweatband configuration.

4. A method of forming a breathable elastic structure according to claim 1 further comprising the step of forming the structure into an undergarment configuration.

5. A method of forming a breathable elastic structure according to claim 1 further comprising the step of forming the structure into a body member support configuration.

6. A method of forming a breathable elastic structure having substantially unidirectional elastic properties, comprising the steps of:

providing a nonwoven low basis weight first breathable outside layer, a nonwoven low basis weight second breathable outside layer, and a first elastic layer having a multiplicity of nonintersecting elastic strands, with the first and second outside layers having a low basis weight of a controlled irregularity;

stretching the first elastic layer by stretching the nonintersecting elastic strands of the first elastic layer;

positioning the stretched nonintersecting elastic strands of the first elastic layer between the first and second outside layers;

adhering the first and second outside layers together with the stretched first elastic layer therebetween to form a substantially unitary structure by bonding together with a controlled irregularity the first and second outside layers; and relaxing the stretching of the first elastic layer to cause the first elastic layer to contract and to draw the outside layers into pleats having a controlled irregularity substantially uniformly distributed throughout the elastic structure, and the pleats, when drawn apart, having substantially unidirectional elastic properties so as to allow the elastic structure to be drawn apart in a direction substantially parallel with at least one the nonintersecting elastic strands.

7. A method of forming a breathable elastic structure having substantially unidirectional elastic properties, comprising the steps of:

providing a nonwoven low basis weight first breathable outside layer, a nonwoven low basis weight second breathable outside layer, and a first elastic layer having a multiplicity of nonintersecting elastic strands;

stretching the first elastic layer by stretching the nonintersecting elastic strands of the first elastic layer;

positioning the stretched nonintersecting elastic strands of the first elastic layer between the first and second outside layers and positioning the nonintersecting elastic strands of the first elastic layer out of parallel;

adhering the first and second outside layers together with the stretched first elastic layer therebetween to form a substantially unitary structure; and relaxing the stretching of the first elastic layer to cause the first elastic layer to contract and to draw the outside layers into pleats having a controlled irregularity and the pleats, when drawn apart, having substantially unidirectional elastic properties so as to allow the elastic structure to be drawn apart in a direction substantially parallel with at least one the nonintersecting elastic strands.

8. A method of forming a breathable elastic structure having substantially unidirectional elastic properties, comprising the steps of:

providing a nonwoven low basis weight first breathable outside layer, a nonwoven low basis weight second breathable outside layer, and a first elastic layer having a multiplicity of nonintersecting elastic strands;

stretching the first elastic layer by stretching the nonintersecting elastic strands of the first elastic layer and by differentially tensioning adjacent nonintersecting elastic strands within the first elastic layer;

positioning the stretched nonintersecting elastic strands of the first elastic layer between the first and second outside layers;

adhering the first and second outside layers together with the stretched first elastic layer therebetween to form a substantially unitary structure; and relaxing the stretching of the first elastic layer to cause the first elastic layer to contract and to draw the outside layers into pleats having a controlled irregularity with the pleats between any two adjacent elastic strands having a different period and amplitude adjacent to one of said two adjacent strands than the period and amplitude adjacent to the other of said two adjacent strands, and the pleats, when drawn apart, having substantially unidirectional elastic properties so as to allow the elastic structure to be drawn apart in a direction substantially parallel with at least one the nonintersecting elastic strands.

9. A method of forming a breathable elastic structure having substantially unidirectional elastic properties, comprising the steps of:

providing a nonwoven low basis weight first breathable outside layer, a nonwoven low basis weight second breathable outside layer, and a first elastic layer having a multiplicity of nonintersecting elastic strands;

stretching the first elastic layer by stretching the nonintersecting elastic strands of the first elastic layer;

positioning the stretched nonintersecting elastic strands of the first elastic layer between the first and second outside layers;

adhering the first and second outside layers together with the stretched first elastic layer therebetween to form a substantially unitary structure, and adhering together the first and second outside layers with the first stretched elastic layer therebetween using an adhesive layer having a predetermined adhesive pattern comprising adhesive areas interspersed with open, nonadhesive areas to provide a controlled irregularity of an adhesive; and relaxing the stretching of the first elastic layer to cause the first elastic layer to contract and to draw the outside layers into pleats having a controlled irregularity and the pleats, when drawn apart, having substantially unidirectional elastic properties so as to allow the elastic stucture to be drawn apart in a direction substantially parallel with at least one the nonintersecting elastic strands.

10. A method of forming a breathable multidirectional elastic structure comprising the steps of:

providing first and second low basis weight nonwoven breathable outside layers, and first and second elastic layers, with each elastic layer comprising plural elastic strands;

applying an adhesive layer to at least one of the first and second outside layers by forming the adhesive layer to have a first group of substantially mutually parallel bands of adhesive and a second group of substantially mutually parallel bands of adhesive, with the first group of adhesive bands intersecting the second group of adhesive bands at an intersection angle;

configuring the elastic strands of the first elastic layer to conform to the first group of adhesive bands, and configuring the elastic strands of the second elastic layer to conform to the second group of adhesive bands;

sandwiching the first and second elastic layers between the first and second outside layers; and bonding together the first and second outside layers, with the elastic strands of the first and second elastic layers sandwiched therebetween, using the adhesive layer.

11. A method of forming a breathable multidirectional elastic structure according to claim 10 further comprising the step of forming the structure into an undergarment configuration.

12. A method of forming a breathable multidirectional elastic structure according to claim 10 further including the step of fixing said intersection angle of the first and second groups of adhesive bands at substantially 90°.

13. A method of forming a breathable multidirectional elastic structure according to claim 10 wherein the providing step comprises selecting the first and second outside layers to have a low basis weight of a controlled irregularity.

14. A method of forming a breathable multidirectional elastic structure according to claim 10 wherein:

the providing step further comprises providing the first elastic layer as comprising a first multiplicity of nonintersecting elastic strands, and providing the second elastic layer as comprising a second multiplicity of nonintersecting elastic strands;

the applying step comprises forming the adhesive layer with each adhesive band of the first group of adhesive bands having a width sufficient to allow the nonintersecting elastic strands of the first elastic layer to be configured out of parallel, and with each adhesive band of the second group of adhesive bands having a width sufficient to allow the nonintersecting elastic strands of the second elastic layer to be configured out of parallel; and the configuring step comprises configuring the first multiplicity of elastic strands of the first elastic layer out of parallel, and configuring the second multiplicity of elastic strands of the second elastic layer out of parallel.

15. A method of forming a breathable multidirectional elastic structure according to claim 10 wherein:

the providing step further includes providing a third elastic layer comprising a plurality of nonintersecting elastic strands;

the applying step further comprises forming the adhesive layer to have a third region of adhesive separate from the first and second groups of adhesive bands;

the configuring step further includes configuring the plurality of nonintersecting strands of the third elastic layer to conform to the adhesive layer in the third region;

the sandwiching step further comprises sandwiching the third elastic layer between the first and second outside layers; and the bonding step further includes bonding the first and second outside layers together with the nonintersecting elastic strands of the third elastic layer sandwiched therebetween using the adhesive layer to form a multidirectional elastic structure having a unidirectional elastic region defined by the location of the third elastic layer of nonintersecting elastic strands.

16. A method of forming a breathable multidirectional elastic structure according to claim 10 wherein the configuring step comprises configuring the elastic strands of the first elastic layer such that each of the adhesive bands of the first group has only one of the elastic strands of the first elastic layer associated therewith, and configuring the elastic strands of the second elastic layer such that each of the adhesive bands of the second group has only one of the elastic strands of the second elastic layer associated therewith.

17. A method of forming a breathable multidirectional elastic structure according to claim 10 further comprising the step of forming the structure into a body member support configuration.

18. A method of forming a breathable multidirectional elastic structure according to claim 10 further comprising the step of configuring at least one layer selected from the group of the first and second outside layers, the adhesive layer, and the first and second elastic layers, to introduce into a surface of the elastic structure a controlled irregularity of pleating which is substantially regularly distributed throughout the multidirectional elastic structure.

19. A method of forming a breathable multidirectional elastic structure according to claim 10 further including the steps of:
before said bonding step, tensioning the elastic strands of the first elastic layer to conform with the first group of adhesive bands;
before said bonding step, tensioning the elastic strands of the second elastic layer to conform with the second group of adhesive bands;
before said bonding step, positioning the tensioned elastic strands of the first and second elastic layers between the first and second outside layers; and
after said bonding step, releasing the tensioning of the elastic strands of the first and second elastic layers to cause the elastic layers to contract and to draw the outside layers into pleats to form soft and breathable opposing outer surfaces.

20. A method of forming a breathable multidirectional elastic structure according to claim 19 wherein:
the step of tensioning the elastic strands of the first elastic layer comprises tensioning the elastic strands of the first elastic layer to a first tension; and
the step of tensioning the elastic strands of the second elastic layer comprises tensioning the elastic strands of the second elastic layer to a second tension which is unequal to the first tension to produce a multidirectional elastic structure having differing elastic properties in different directions along the outer surfaces of the structure.

21. A method of forming a breathable multidirectional elastic structure according to claim 19 wherein:
the step of tensioning the elastic strands of the first elastic layer comprises tensioning adjacent elastic strands to unequal tensions; and
the step of tensioning the elastic strands of the second elastic layer comprises tensioning adjacent elastic strands to unequal tensions, whereby the controlled irregularity of pleating is introduced into a surface of the elastic structure.

22. A method of forming a breathable elastic structure having substantially multidirectional elastic properties, comprising the steps of:
providing a nonwoven low basis weight first breathable outside layer, a nonwoven low basis weight second breathable outside layer, a first elastic layer having a first multiplicity of nonintersecting elastic strands, and a second elastic layer having a second multiplicity of nonintersecting elastic strands;
stretching the first and second elastic layers by stretching the first multiplicity of nonintersecting elastic strands and by stretching the second multiplicity of nonintersecting elastic strands;
first positioning the stretched first layer between the first and second outside layers;
after the first positioning step, positioning the stretched second elastic layer between the first and second outside layers with the elastic strands of the second layer intersecting the elastic strands of the first layer;
adhering the first and second outside layers together with the stretched first and second elastic layers therebetween to form a substantially unitary structure; and
forming a breathable elastic structure having a nonuniformity which is substantially regularly distributed throughout the elastic structure, the forming step comprising the step of relaxing the stretching of the first and second elastic layers to cause the first and second elastic layers to contract and to draw the outside layers into pleats having a controlled irregularity and the pleats, when drawn apart, having substantially multidirectional elastic properties so as to form an elastic structure having elastic properties in more than one direction.

23. A method of forming a breathable elastic structure having substantially unidirectional elastic properties, comprising the steps of:
providing a nonwoven low basis weight first breathable outside layer, a nonwoven low basis weight second breathable outside layer, and a first elastic layer having a multiplicity of nonintersecting elastic strands;
stretching the first elastic layer by stretching the nonintersecting elastic strands of the first elastic layer;
positioning the stretched nonintersecting elastic strands of the first elastic layer between the first and second outside layers;
adhering the first and second outside layers together with the stretched first elastic layer therebetween to form a substantially unitary structure;
forming a breathable elastic structure having a nonuniformity which is substantially regularly distributed throughout the elastic structure, the forming step comprising the step of relaxing the stretching of the first elastic layer to cause the first elastic layer to contract and to draw the outside layers into pleats having a controlled irregularity and the pleats, when drawn apart, having substantially unidirectional elastic properties so as to allow the elastic structure to be drawn apart in a direction substantially parallel with at least one the nonintersecting elastic strands; and
forming the structure into a strap configuration.

24. A method of forming a breathable elastic structure having substantially multidirectional elastic properties, comprising the steps of:
providing a nonwoven low basis weight first breathable outside layer, a nonwoven low basis weight second breathable outside layer, a first elastic layer having a first multiplicity of nonintersecting elastic strands, and a second elastic layer having a second multiplicity of nonintersecting elastic strands;
stretching the first and second elastic layers by stretching the first multiplicity of nonintersecting elastic strands and by stretching the second multiplicity of nonintersecting elastic strands;
positioning the stretched first and second elastic layers between the first and second outside layers, with the elastic strands of the first layer intersecting the elastic strands of the second layer;
adhering the first and second outside layers together with the stretched first and second elastic layers therebetween to form a substantially unitary structure by adhering the structure with an adhesive layer having a predetermined adhesive pattern comprising adhesive areas interspersed with open, nonadhesive areas; and
forming a breathable elastic structure having a nonuniformity which is substantially regularly distributed throughout the elastic structure, the forming step comprising the step of relaxing the stretching of the first and second elastic layers to cause the first and second elastic layers to contract and to draw the outside layers into pleats having a controlled irregularity with the pleats on opposing sides of each elastic strand substantially having different periods and amplitudes, and the pleats, when drawn apart, having substantially multidirectional elastic properties so as to form a multidirectional elastic structure having elastic properties in more than one direction.

25. A method of forming a breathable elastic structure having substantially unidirectional elastic properties, comprising the steps of:

providing a nonwoven low basis weight first breathable outside layer, a nonwoven low basis weight second breathable outside layer, and a first elastic layer having a multiplicity of nonintersecting elastic strands;

stretching the first elastic layer by stretching the nonintersecting elastic strands of the first elastic layer;

positioning the stretched nonintersecting elastic strands of the first elastic layer between the first and second outside layers;

adhering the first and second outside layers together with the stretched first elastic layer therebetween to form a substantially unitary structure by spraying an adhesive layer on at least one of the first and second breathable outside layers; and forming a breathable elastic structure having a nonuniformity which is substantially regularly distributed throughout the elastic structure, the forming step comprising the step of relaxing the stretching of the first elastic layer to cause the first elastic layer to contract and to draw the outside layers into pleats having a controlled irregularity and the pleats, when drawn apart, having substantially unidirectional elastic properties so as to allow the elastic structure to be drawn apart in a direction substantially parallel with at least one the nonintersecting elastic strands.

26. A method of forming a breathable elastic structure comprising the steps of:

providing a nonwoven low basis weight first breathable outside layer, a nonwoven low basis weight second breathable outside layer, and a first elastic layer having a multiplicity of nonintersecting elastic strands;

stretching the first elastic layer by stretching the elastic strands of the first elastic layer;

positioning the stretched first elastic layer between the first and second outside layers;

adhering the first and second outside layers together with the stretched first elastic layer therebetween to form a substantially unitary structure by screen printing an adhesive layer on at least one of the first and second outside layers; and relaxing the stretching of the first elastic layer to cause the first elastic layer to contract and to draw the outside layers into pleats having a controlled irregularity with the pleats on opposing sides of each elastic strand substantially having different periods and amplitudes and the pleats, when drawn apart, having elastic properties.

* * * * *